United States Patent
Apicella et al.

(10) Patent No.: US 6,743,607 B2
(45) Date of Patent: Jun. 1, 2004

(54) PRODUCTION OF COMPLEX CARBOHYDRATES

(75) Inventors: Michael A. Apicella, Solon, IA (US); Bradford W. Gibson, Berkeley, CA (US); Nancy J. Phillips, Oakland, CA (US)

(73) Assignees: The Regents of the University of California, Oakland, CA (US); The University of Iowa Research Foundation, Iowa City, IA (US)

(*) Notice: Subject to any disclaimer, the term of this patent is extended or adjusted under 35 U.S.C. 154(b) by 59 days.

(21) Appl. No.: 09/991,374

(22) Filed: Nov. 16, 2001

(65) Prior Publication Data

US 2004/0058448 A1 Mar. 25, 2004

Related U.S. Application Data

(63) Continuation of application No. PCT/US00/13538, filed on May 18, 2000.
(60) Provisional application No. 60/134,756, filed on May 18, 1999.

(51) Int. Cl.$^7$ .............................. C12P 19/04; C12N 1/21
(52) U.S. Cl. ............... 435/101; 435/252.3; 435/252.33; 424/257.1; 424/249.1; 424/256.1; 424/258.1
(58) Field of Search .................. 435/252.33, 252.3, 435/101; 424/257.1, 249.1, 256.1, 258.1

(56) References Cited

U.S. PATENT DOCUMENTS

| | | | |
|---|---|---|---|
| 4,703,008 A | 10/1987 | Lin | 435/240.2 |
| 4,745,051 A | 5/1988 | Smith et al. | 435/68 |
| 5,308,460 A | 5/1994 | Mazid et al. | 204/180.1 |
| 5,370,872 A | 12/1994 | Cryz et al. | 424/194.1 |
| 5,705,367 A | 1/1998 | Gotschlich | 435/97 |
| 5,736,533 A | 4/1998 | Simon et al. | 514/61 |
| 5,747,326 A | 5/1998 | Gerardy-Schahn et al. | 435/240.2 |
| 5,945,322 A | 8/1999 | Gotschlich | 435/193 |
| 5,955,347 A | 9/1999 | Lowe | 435/252.3 |

OTHER PUBLICATIONS

Abu Kwaik et al (Molecular Microbiology 5(10):2475–2480 (1991)).*
Westphal et al (Methods in Carbohydrate Chemistry, Whistler et al, eds., vol. 5, pp. 83–91, Academic Press, New York (1984)).*
Brade et al (Infection and Immunity 55(2):482–486 (1987)).*
Alexander, D.C., et al., "Role of the rfe Gene in the Biosynthesis of the *Escherichia coli* O7–Specific Lipopolysaccharide and Other O–Specific Polysaccharides Containing N–Acetylglucosamine", *Journal of Bacteriology*, 176(22), 7079–7084, (Nov. 1994).
Andersson, S.G., et al., "The Genome sequence of *Rickettsia prowazekii* and the origin of mitochondria", *Nature*, 396, pp. 133–140, (Nov. 12, 1998).
Bozue, J.A., et al., "*Haemophilus ducreyi* Produces a Novel Sialyltransferase", *The Journal of Biological Chemistry*, 274 (7), pp. 4106–4114, (Feb. 12, 1999).
Bugert, P., et al., "Molecular analysis of the ams operon required for exopolysaccharide synthesis of *Erwinia amylovora*", *Molecular Microbiology*, 15 (5), pp. 917–933, (1995).
Comstock, L.E., et al., "Analysis of a Capsular Polysaccharide Biosynthesis Locus of *Bacteriodes fragilis*", *Infection and Immunity*, 67 (7), pp. 3525–3532, (Jul. 1999).
Darveau, R.P., et al., "Procedure for Isolation of Bacterial Lipopolysaccharides from Both Smooth and Rough *Pseudomonas aeruginosa* and *Salmonella typhimurium* strains", *Journal of Bacteriology*, 155(2), 831–838, (Aug. 1983).
Gibson, B.W., et al., "Characterization of Bacterial Lipooligosaccharides by Delayed Extraction Matrix–Assisted Laser Desorption Ionization Time–of–Flight Mass Spectrometry", *J. Am. Soc. Mass. Spectrom.*, 8 (6), pp. 645–658, (Jun. 1997).
Gilbert, M., et al., "Cloning of the Lipooligosaccharide alpha–2,3–Sialyltransferase from the Bacterial Pathogens *Neisseria meningitidis* and *Neisseria gonorrhoeae*", *The Journal of Biological Chemistry*, 271 (45), pp. 28271–28276, (Nov. 6, 1996).
Gotschlich, E.C., "Genetic Locus for the Biosynthesis of the Variable Portion of *Neisseria gonorrhoeae* Lipooligosaccharide", *J. Exp. Med.*, 180, pp. 2181–2190, (Dec. 1994).
Grunden, A.M., et al., "Repression of the *Escherichia coli* modABCD (Molybdate Transport) Operon by ModEt", *Journal of Bacteriology*, 178 (3), pp. 735–744, (Feb. 1996).
Holst, O., et al., "Structural analysis of the heptose/hexose region of the lipopolysaccharide form *Escherichia coli* K–12 strain W3100", *Carbohydrate Res.*, 215 (2), pp. 323–335, (1991).
Jennings, M.P., et al., "Molecular analysis of a locus for the biosynthesis and phase–variable expression of the lacto–N–neotetraose terminal lipopolysaccharide structure in *Neisseria meningitidis*", *Molecular Microbiology*, 18 (4), pp. 729–740, (1995).
Kwaik, Y.A., et al., "Analysis of *Haemophilus influenzae* Type b Lipooligosaccharide–Synthesis Genes that Assemble or Expose a 2–keto–3–deoxyoctulosonic Acid Epitope.", *Molecular Microbiology*, 5(10), 2475–2480, (Oct. 1991).

(List continued on next page.)

Primary Examiner—Francisco C Prats
(74) Attorney, Agent, or Firm—Fish & Richardson P.C., P.A.

(57) ABSTRACT

Compositions and methods for making complex carbohydrates in a bacterial production cell are disclosed. The complex carbohydrates that can be made include oligosaccharides and polysaccharides of bacterial or mammalian origin.

7 Claims, 3 Drawing Sheets

OTHER PUBLICATIONS

Marolda, C.L., et al., "Genetic Analysis of the dTDP–Rhamnose Biosynthesis Region of the *Escherichia coli* VW187 (O7:K1) rfb Gene Cluster: Identification of Functional Homologs of rfbB and rfbA in the rff Cluster and Correct Location of the rffE Gene", *Journal of Bacteriology, 177* (*19*), pp. 5539–5546, (Oct. 1995).

McLaughlin, R., et al., "Characterization and Sequence Analysis of the lsg (LOS Synthesis Genes) Locus from *Haemophilus influenzae* type b", *Journal of Endotoxin Res., 1*, 165–174, (1994).

Nakano, Y., et al., "A gene cluster for 6–deoxy–L–talan synthesis in *Actinobacillus actinomycetemcomitans*", *Biochimica et Biophysica Acta, 1442*, pp. 409–414, (1998).

Phillips, N.J., et al., "Characterization of Chimeric Lipopolysaccharides from *Escherichia coli* Strain JM109 Transformed with Lipooligosaccharide synthesis genes (isg) from *Haemophilus influenzae*", *J. of Biol. Chem., 275* (*7*), pp. 4747–4758, (Feb. 16, 2000).

Phillips, N.J., et al., "Characterization of Two Transposon Mutants from *Haemophilus influenzae* Type b with Altered Lipooligosaccharide Biosynthesis", *Biochemistry, 35*, pp. 5937–5947, (1996).

Risberg, A., et al., "Structural analysis of the lipopolysaccharide oligosaccharide epitopes expressed by a capsule–deficient strain of *Haemophilus influenzae* Rd", *Eur. J. of Biochem., 261* (*1*), pp. 171–180, (Apr. 1999).

Skurnik, N., et al., "A novel locus of *Yersinia enterocolitica* serotype 0:3 involved in lipopolysaccharide outer core biosynthesis", *Molecular Microbiology, 17* (*3*), pp. 575–594, (1995).

Spinola, S.M., et al., "Cloning and Expression in *Escherichia coli* of a *Haemophilus influenzae* Type b Lipooligosaccharide Synthesis Gene(s) that Encodes a 2–Keto–3–Deoxyoctulsonic Acid Epitope", *Infection and Immunity, 58*(*6*), 1558–1564, (Jun. 1990).

Sussking, M., et al., "Identification of a Novel Heptoglycan of alpha–1–2–Linked d–glycero–d–manno–heptopyranose. Chemical and antigenic structure of lipopolysaccharides from *Klebsiella pneumoniae ssp.* Pneumoniae rough strain R20", *J. of Biol. Chem., 273* (*12*), pp. 7006–7017, (Mar. 1998).

Wang, G., et al., "Characterization of *Rhodobacter capsulatus* Genes Encoding a Molybdenum Transport Systemand Putative Molybdenum–Pterin–Binding Proteins", *Journal of Bacteriology, 175* (*10*), pp. 3031–3042, (May 1993).

Yao, Z., et al., "Genetic Analysis of the O–Specific Lipopolysaccharide Biosynthesis Region (rfb) of *Escherichia coli* K–12 W3110: Identification of Genes That Confer Group 6 Specificity to *Shigella flexneri* Serotypes Y and 4at", *Journal of Bacteriology, 176* (*13*), pp. 4133–4143, (Jul. 1994).

Yoshida, Y., et al., "Identification of a Genetic Locus Essential for Serotype b–Specific Antigen Synthesis in *Actinobacillus actinomycetemcomitans*", *Infection and Immunity, 66*(*1*), pp. 107–114, (Jan. 1998).

Zhang, L., et al., "Molecular and chemical characterization of the lipopolysaccharide O–antigen and its role in the virulence of *Yersinia enterocolitica* serotype 0:8", *Molecular Microbiology, 23* (*1*), pp. 63–76, (1997).

Preston, Andrew, et al., "The Lipooligosaccharides of Pathogenic Gram–Negative Bacteria", *Critical Reviews in Microbiology, 22*, (1996),139–180.

Swierzko, Anna, et al., "Specificity of Rabbit Antisera against the Rough Lipopolysaccharide of *Salmonella minnesota* R4", Infections and Immunity vol. 6 No. 8, (Aug. 1993),3316–3221.

* cited by examiner

**(A) Lipooligosaccharide synthesis genes (*lsg*)**

(B) Transposon inserts

(C) Chimeric transformants

*E. coli* r-LPS pGEM

Glcα1→3Glcα1→3Hepα1→3Hepα1→5Kdo

R →7Hepα1→6Glcα1→2Glcα1→3Glcα1→3Hepα1→3Hepα1→5Kdo

Chimeric LPS   R = pGEMLOS-7 pGEMLOS-5 pGEMLOS-4

PRODUCTION OF COMPLEX CARBOHYDRATES

CLAIM OF PRIORITY

This application is a continuation under 35 U.S.C. 111(a) of International Application No. PCT/US00/13538 filed May 18, 2000 and published as WO 00/70060 on Nov. 23, 2000, which claims priority under 35 U.S.C. 119(e) from U.S. Provisional Application Serial No. 60/134,756, filed May 18, 1999, which applications are is incorporated herein by reference.

GOVERNMENTAL RIGHTS

The United States Government retains certain rights in this invention Financial support was provided by the National Institute of Allergy and Infectious Diseases under Grant Number A124016 and from the NIH National Center for Research Resources under Grants Number RRO1614 and RRO4112.

FIELD OF THE INVENTION

This invention relates to a method for the production of complex carbohydrates on an LPS backbone structure in Gram-negative bacteria.

BACKGROUND OF THE INVENTION

Complex carbohydrates occur in nature and are involved in a wide array of biological functions, including viral, bacterial and fungal pathogenesis, cell-to-cell and intracellular recognition, binding of hormones and pathogens to cell-surface receptors and in antigen-antibody recognition. The term "complex carbohydrates" embraces a wide array of chemical compounds having the general formula $(CH_2O)_n$ where the monomer unit is selected from any of thousands of naturally occurring or synthetic monomers, including, but not limited to, glucose, galactose, mannose, fucose and sialic acid Saccharides may have additional constituents such as amino, sulfate or phosphate groups, in addition to the carbon-hydrogen-oxygen core. The polymer consisting of two to ten saccharide units is termed an oligosaccharide (OS) and that consisting of more than ten saccharide units is termed a polysaccharide (PS). These monosaccharide building blocks can be linked in at least 10 different ways, leading to an astronomical number of different combinations and permutations. It is found that strains within species and even tissue within an organism differ in complex carbohydrate structure. This high degree of variability, the highly specific composition of naturally occurring complex carbohydrates and the wide range of biological roles make these compounds especially significant.

Gram-negative bacteria contain complex carbohydrates, which are linked to lipids to form lipooligosaccharides (LOS) or lipopolysaccharides (LPS.) The immunogenicity of the LOS and LPS resides in the carbohydrate moiety, while pathogenicity resides in the lipid moiety. For this reason, OS and PS are useful as vaccines against Gram-negative pathogens and for identification of gram-negative bacteria.

U.S. patent application Ser. No. 5,736,533 discloses oligosaccharides useful as therapeutic agents against pathogens that are the causative agents of respiratory infections. It is believed that pathogenic bacteria are able to colonize tissue by binding to carbohydrates on the surface of the tissue and that providing an excess of specific soluble oligosaccharides can result in competitive inhibition of bacterial colonization.

OS and PS from LPS and LOS can be produced by growing the specific bacterial pathogen in culture, with subsequent cleavage of the lipid moiety and purification However, most pathogenic bacteria are fastidious in their growth requirements and slow growing, making this mode of production impractical. For example, *Haemophilus influenzae* is known to require a carbon dioxide atmosphere and brain/heart extract for growth *Helicobacter pylori* grows very poorly in broth cultures required for OS and PS production. In addition, many of these bacterial pathogens (for example, *Neisseria meningitidis*) can be dangerous to grow in large volumes because of the risk of aerosol and possible infection spread. The ability to produce the OS and PS structures of fastidious bacterial pathogens in bacterial strains such as *Escherichia coli* and *Salmonella Minnesota* which grow rapidly to high density offers a rapid way to produce these OS and PS from fastidious bacterial pathogens.

Eucaryotic proteins and peptides frequently have carbohydrate moieties on their surfaces, which act as specific binding sites for hormones, which are also glycosylated, that is, have complex carbohydrates linked to the peptide structure. Moreover, in addition to the recognition role, carbohydrates are necessary to the proper three-dimensional folding of polypeptides into functional glycoproteins. Bacteria do not glycosylate peptides and proteins efficiently or in a manner equivalent to that of eucaryotes. For that reason, although bacteria are widely used as production cells for growing eucaryotic peptides and proteins, such useful human glycopeptides such as erythropoetin are grown in mammalian cells. U.S. Pat. No. 4,703,008 discloses a method for the production of erythropoietin, in which cells such as Chinese hamster ovary cells are transfected with the DNA coding for the hormone and grown under a carbon dioxide atmosphere in complex medium. The resulting hormone is sufficiently similar to the naturally occurring hormone to be effective as a therapeutic for human use.

An additional utility for isolated, cell-specific carbohydrates is for competitive inhibition of disease agents in which infection is reliant on surface-recognition glycosylated proteins. For example, the human immunodeficiency virus is known to bind to the surface receptor on T-4 lymphocytes. If an excess of free T-4 receptor carbohydrate is present in the bodily fluids of the patient, the virus will bind to the free carbohydrate and is effectively prevented from infecting the T-4 lymphocyte.

Competitive inhibition of binding of antibodies to cell surfaces by administration of cell-recognition molecules may have therapeutic potential in the treatment of autoimmune diseases such as lupus erythematosus, multiple sclerosis and rheumatoid arthritis. Such molecules may bind to the cell receptor, blocking the binding of the autoimmunie antibodies which cause the degeneration seen in such disease states.

U.S. Pat. No. 4,745,051 discloses a method for expressing DNA in an insect cell, a method that has practical application for the production of glycosylated peptides and proteins. However, the glycosylation resulting is that native to the insect, consisting of higher levels of mannose than are typical of mammalian cells.

Practical production of peptides and polypeptides in bacterial production cells is well established. Chemical and enzymatic means for glycosylating peptides and proteins are well known in the art For example, U.S. Pat. No. 5,370,872 discloses a method for coupling PS through a carboxyl or hydroxyl group to a protein. Classic organic syntheses of complex carbohydrates have long been known, but with limited practical application. In addition to the difficulties inherent in the complexity of the glycopolymer molecule, many glycosidic bonds are labile and must be protected and deprotected during chemical synthesis, adding to the difficulty of synthesis and reducing the yield of product.

Because of the drawbacks of organic synthesis, enzymatic synthesis has been devised. It is known that glycosylation proceeds by the step-wise addition of monomers through the action of such enzymes as glycosyltransferases. The reaction products can be further modified by lysases, acetylases, sulflases, phosphorylases, kinases, epimerases, methylases, transferases and the like. U.S. Pat. No. 5,308,460 discloses such a step-wise synthesis on an immobilized matrix.

A need remains for a more efficient and practical method for the production of complex carbohydrates, and glycoproteins and glycopeptides containing complex carbohydrates specific to a species or tissue.

SUMMARY OF THE INVENTION

The present invention is directed to the production of complex carbohydrates in a production cell. It is here disclosed that certain bacteria, such as *Escherichia coli* Strain K-12, have a core liposaccharide with a terminal heptose. A suitable production cell also contains an enzyme which catalyzes the transfer to the terminal heptose of an acceptor molecule, such as N-acetylglucosamine, to form a "scaffold" upon which glycosyltransferases add other saccharide monomers to form complex carbohydrates. If an otherwise suitable production cell lacks such an enzyme, the DNA encoding the gene rfe (UDP-GlcNAc:Undecaprenol GlcNAc-1 phosphate transferase) of *Haemophilus influenzae* may be inserted into the production cell. Preferably, production of rfe is enhanced by the presence of the gene products of the gene lsgG. By inserting genes encoding glyeotransferase glycosyltransferases into the production cell, the complex carbohydrates specific to bacteria such as *Haemophilus influenzae*, Neisseria spp, Salmonella spp and *Escherichia coli* are produced. Mammalian complex carbohydrate such polysialyl can also be produced.

Accordingly, the invention provides a process for the production of a complex carbohydrate which comprises the steps of: (a) inoculating transformed production cells into a culture medium capable of supporting the growth of said production cells wherein said production cells are prepared by transforming bacteria comprising (i) a core lipid structure containing a terminal heptose molecule and (ii) an enzyme capable of adding an acceptor molecule to said heptose molecule by inserting an isolated DNA sequence encoding glycotransferase synthesizes a complex carbohydrate into said bacteria to yield transformed production cells; (b) allowing growth of said transformed production cells; and (c) recovering said complex carbohydrate from the culture medium.

The invention also provides a process for the production of an oligosaccharide which comprises the steps of: (a) transforming gram-negative bacteria comprising (i) a core lipid structure containing a terminal heptose and (ii) an enzyme that adds a galactose molecule to said heptose wherein said transformed gram-negative bacteria are prepared by constructing a vector comprising an isolated DNA sequence coding for a glycotransferase that synthesizes an oligosaccharide; (b) inoculating said transformed gram-negative bacteria into a culture medium capable of supporting the growth of said transformed bacteria; (c) allowing growth of said inoculated gram-negative bacteria; and (d) recovering said oligosaccharide from the culture medium.

Using methods disclosed in this application, a production cell suitable for the practical production of other complex carbohydrates can be identified. Such a suitable production cell will have an acceptor molecule specific to the carbohydrate to be synthesized, or a site that can be modified to add such a specific acceptor molecule. The production cell will contain the initiating IsgG or IsgF to form the appropriate acceptor. DNA coding for the glycotransferases of other species, strains, tissues, hormones, receptors or other cell-surface carbohydrates can then be inserted into such a production cell, with the resultant production of oligosaccharides or polysaccharide specific to that species, strain, tissue, hormone, receptor or other cell-surface carbohydrate. The nucleotide sequences for the genes rfc and lsG are on file in the *H. influenzae* Rd database available from TIGR (Bethesda, Md). Sequences for glycotransferases are available from the references herein disclosed.

Also provided are methods for separating and purifying the product.

The invention also provides a process for the production of a complex carbohydrate, comprising culturing production cells comprising a chimeric DNA sequence encoding a glycotrnnsferase, so as to yield production cells comprising an altered level of complex carbohydrate, wherein the production cells are bacteria comprising a core lipid structure containing a terminal heptose molecule and encoding an enzyme capable of adding an acceptor molecule to the heptose molecule. The invention also provides a process further comprising recovering the complex carbohydrate.

DETAILED DESCRIPTION OF THE INVENTION

Figure 1:
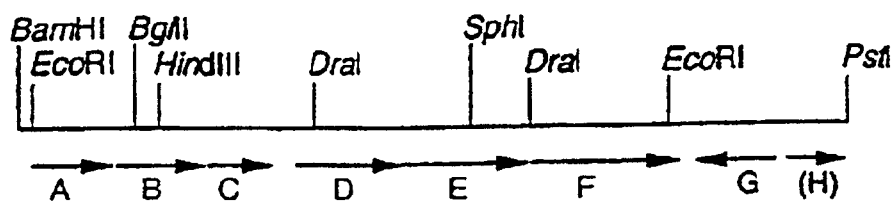
FIG. 1: The lsg region of *Haemophilus influenzae* DNA. (A) Diagram of the eight orfs. (B) Locations of m-Tn3(Cm) insertion sites (6). (C) Restriction maps of the EMBLOS-1 subclones that modified the *E. coli* JM 109 LPS.
Figure 1:
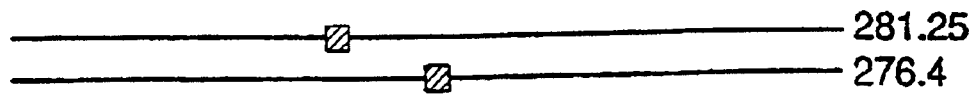
Figure 1:
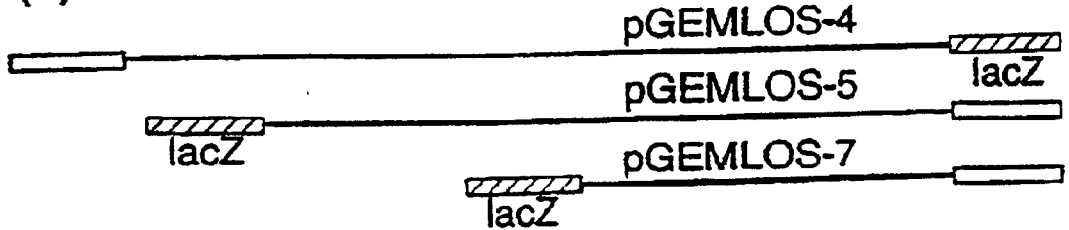

The present invention provides a method by which the terminal heptose of the core structure of any gram bacterial species which contains the gene rfe (UDP-GlcNAc:Undecaprenol GlcNAc-1 phosphate transferase) (Alexander et al. (1994) J. Bacteriol., 176-7079–7084) can be modified so as to act as an acceptor for oligosaccharide synthesis. The rfe gene encodes for a protein which catalyzes the transfer of N-acetyl glucosamine (GlcNAc, an "acceptor molecule") onto the carrier lipid undecaprenol phosphate. The regulation of this gene can be controlled with a regulatory gene, lsgG, identified in *Haemophilus influenzae*. The increase in rfe expression caused by lsgG mediates the deposition of a GlcNAc residue on the terminal heptose of LPS and LOS from a variety of gram-negative bacterial species including *E. coli, Salmonella Minnesota* and *H. influenzae*. This GlcNAc has been found to function as an acceptor molecule forming a scaffold for the sequential addition of saccharide monomers, under the direction of glycotransferases. For example, the galactosyltrnsferase gene, lsgF, results in the addition of a galactose to the GlcNAc. The gene sequence coding for the lsg glycotransferases of *H. influenzae* has been inserted into an *Escherichia coli* K-12 strain production cell, with the resultant production of *H. influenzae*-specific LOS epitopes in *E. coli*.

Any production cell containing an initiating enzyme similar to rfe can add an appropriate acceptor to form the scaffold. The production will preferably also contain the regulatory gene lsgG. DNA coding for the glycotransfees of other species, strains, tissues, hormones, receptors or other cell-surface carbohydrates can then be inserted into such a production cell, with the resultant production of oligosaccharides or polysaccharidea specific to that species, strain, tissue, hormone, receptor or other cell-surface carbohydrate.

Definitions:

Complex carbohydrates: any polymer of formula $(CH_2O)_n$, where n equals at least three monomer units, including polymers with additional substituents including but not limited to $SO_4$, $PO_4$, $CO_4$, $CH_3$, $NH_4$, and such polymers linked to lipids, peptides and proteins.

Production cell: A production cell useful in this invention is defined as any bacterium which contains an LPS or LOS-saccharide inner core terminating in a molecule and containing an enzyme capable of adding an acceptor molecule to the terminal molecule to serve as a scaffold for elongation and which can be transformed with exogenous DNA coding for glycosyltransferases. Cells that are otherwise suitable but lack the proper acceptor molecule may be used as production cells if they are cotransformed with genes such as rfe and lsgG, to appropriately modify the LPS or LOS to function as an acceptor molecule for the formation of a scaffold.

Hib production cell: the preferred cell for production of *H. influenzae* type B-specific OS is preferably a gram-negative bacteriuim, most preferably *E. coli* K-12 strain JM 109.

Synthetic gene(s): the DNA coding for the enzyme or enzymes that synthesize the desired complex carbohydrate. These genes include those coding for glycotransferases, lyases, acetylases, sulfatases, phosphorylases, kinases, epimerases, methylases and the like.

EXAMPLE 1

Selection of a Hib Production Cell

Capsular strains of *Haemophilus influenzae* type b (Hib) are responsible for various invasive and bacteriuim infections in humans, including meningitis and pneumonia. The surface lipooligosaccharides (LOS) of Hib are known to be important factors in microbial virulence and pathogenesis. Structural studies of Hib LOS from wild-type and mutant strains have shown that the LOS contains a conserved heptose trisaccharide core which can be extended with additional sugars on each heptose. Recently, a revised structure of the *E. coli* K-12 core region was reported which also contains a heptose trisaccharide inner core and a fourth heptose present on the terminus of the main oligosaccharide branch:

| Gal$\alpha$ 1 | Hep$\alpha$ 1 |
|---|---|
| ↓ | ↓ |
| 6 | 7 |
| Hep$\alpha$1 → 6Glc$\alpha$1 → 2Glc$\alpha$1 → +3Glc$\alpha$1 → 3Hep$\alpha$1 → 3Hep$\alpha$1 → 5Kdo | |

Previous work showed that the core region of *E. coli* transformed with synthetic enzyme genes could be elongated by the addition of saccharide monomers under the direction of *H. influenzae* genes to produce a modified *E. coli* LPS that was elongated by approximately five monomer unit. It was thought that the monomers were added at each of the heptose& (Kwaik et al., Molecular Microbiology, 5:2475–2480 (1990).) Therefore, efforts were made to transform an *E. coli* K-12 strain termed JM109 with *H. influenzae* synthesis genes in an attempt to determine whether an LOS substantially identical to that of *H. influenzae* could be produced. *Escherichia coli* strains were routinely cultured at 37° C. using LB agar or broth with appropriate antibiotics. Vectors used in these studies were previously described. (Kwaik et al. (1990)). LPS from *E. coli* JM 109 was prepared by the extraction procedure of Darveau and Hancock (Darveau et al. J. Bacteriol. 155(2), 831–838 (1983).) The LPS was separated by SDS-PAGE in resolving gels containing 15% acrylamide, and visualized by silver staining.

To determine the structure of this chimeric LPS, a few milligrams of LPS from each sample were treated with anhydrous hydrazinc at 37° C. for 20 minutes, and then precipitated with cold acetone.

In order to establish the chemical structure of the *E. coli* core and determine the *E. coli* acceptor residue, the LPS from *E. coli* strain JM 109 was partially characterized using composition analysis, linkage analysis, and mass spectrometry as described in Example 6 below.

2. Isolation of the LOS Synthetic Genes From Hib

Hib strain A-2 was originally isolated from the spinal fluid of a child with meningitis Hib A-2 was grown on chocolate agar supplemented with amino acids and vitamins or brain heart infusion agar supplemented with 4% Fildes reagent (Difco Laboratories, Detroit) at 35° C. in 5% $CO_2$ atmosphere.

A gene cluster from Hib strain A-2 containing LOS synthesis genes (lsg) was previously cloned. (Kwaik et al, (1990). The lsg loci are contained within a 7.4 kb DNA fragment, consisting of seven complete open reading frames (orfs). This region is one of several distinct loci also found in the genome sequence of Hib strain Rd which has been associated with lipopolysaccharide (LPS) biosynthesis.

DNA from the lsg region of Hib strain A-2 was used to construct a genomic library in the lambda bacteriophage EMBL3 (Kwaik et al, 1990)). Twenty six phage clones were prepared which expressed Hib LOS oligosaccharide epitopes in *E. coli* strain LE392. The phage transformant designated EMBLOS-I produced a chimeric LPS with a 1.4 kDa oligosaccharide added to the 4.1 kDa LPS of *E. coli* LE392. Monoclonal antibody (MAb) 6E4, which recognizes two components in the Hib A2 LOS mixture, also recognized the novel 5.5 kDa component in the chimeric LPS, indicating some immunochemical similarity to Hib LOS.

EXAMPLE 3

Transformation of the Hib Production Cell

Restriction fragments of EMBLOS-I were used to make a series of plasmids which modified *E. coli* strain JM 109 to give clones which produced a proposed chimeric series of higher mass LPS species. The transformants termed pGEMLOS-4, pGEMLOS-5, and pGEMLOS-7 generated modified or chimeric LPS of 5.5, 5.1, and 4.5 kDa, respectively. All three apparently modified the 4.1 kDa LPS species from *E. coli*, although only the LPS from pGEMLOS-4 expressed the 6E4 epitope. The LPS from strain pGEMLOS-5 was found to react positively with MAb 3F 11, suggesting the presence of terminal N-acetyllactosamine. The epitope recognized by MAb 6E4 is also present in the LOS of *H. influenzae* nontypable strain 2019, as well as the LPS from *Salmonella Minnesota* Re mutant Binding of this monoclonal antibody to *H. influenzae* LOS can be inhibited by Kdo and the Kdo trisaccharide from the Re mutant of *S. Minnesota*. Because the 6E4 epitope has been associated with the core of Haemophilus LOS, it was originally proposed that the chimeric structures expressed in *E. coli* might arise from the addition of a Haemophilus core structure to an acceptor residue of the *E. coil* 4.1 kDa LPS species.

The Hib production cell was transformed with the plasmid pGEM3Zf+ into which different DNA restriction fragments from *H. influenzae* strain A-2 lsg locus had been ligated (see Table 1 and FIG. 1). The plasmid pGEMLOS-4 contained a 7.4 kb bamhl-pstl fragment of DNA which contained all seven open reading frames (A–G) comprising the lsg locus. The plasmid pGEMLOS-5 contained a 5.5 kb Hind lll-pstl fragment of DNA comprising 5 open reading frames (C–G) of the lsg. The plasmid pGEMLOS-7 contained a 2.8 kb sphl-pstl fragment of DNA comprising 2 open reading frames (F–G) of the lsg locus. The plasmid pGEM3zf+ without an insert was also transformed into strain JM 109. This strain and the LPS isolated from it were termed PGEM.

EXAMPLE 4

Isolation and Purification of Olihsaccharides

The LPS from PGEM (31 mg), pGEMLOS-4 (25 mg), pGEMLOS-5 (15 mg), and pGEMLOS-7 (4.4 mg) was hydrolyzed in 1% acetic acid (2 mg LPS/ml) for 2 hours at 100° C. The hydrolysates were centrifuged at 5000 g for 20 min at 4° C. and the supernatants removed. The pellets were washed with 2 ml of $H_2O$ and centrifuged again (5000 g, 20 min, 4° C.). The supernatants and washings were pooled and lyophilized to give the oligosaccharide fractions. As a standard, 10 mg of LPS from *Salmonella typhimurium* TV 119 Ra mutant (Sigma, St. Louis) was treated in the same fashion.

To prepare desalted oligosaccharide pools for ESI-MS analysis, small aliquots of the crude oligosaccharide fractions (<2 mg) were chromatographed on two Bio-Select SEC 125-5 HPLC columns (Bio-Rad, Richmond, Calif.) connected in series, using 0.05 M pyridinium acetate (pH 5.2) at a flow rate of 1 ml/min. A refractive index detector was used to monitor column effluent and chromatograms were recorded and stored with an integrator.

For large scale separations, the oligosaccharide fractions from PGEM (10.2 mg), pGEMLOS-4 (9.3 mg), and pGEMLOS-5 (7.0 mg) were dissolved in 0.3 ml of 0.05 M pyridinium acetate buffer (pH 5.2) and centrifuge-filtered through a 0.45 gm Nylon-66 membrane. The PGEM and pGEMLOS-4 samples were applied to a single Bio-Gel P-4 column (1.6×84 cm, <400 mesh; BioRad), and the pGEMLOS-5 sample was applied to two Bio-Gel P-4 columns connected in series (1.6×79 cm and 1.6×76.5 cm). The columns were equipped with water jackets maintained at 30° C. Upward elution at a flow rate of 10 ml/h was achieved with a P-1 peristaltic pump (Pharmacia, Piscataway). Effluent was monitored with refractive index and fractions were collected at 10 minute intervals and evaporated to dryness in a concentrator.

EXAMPLE 5

Dephosphorylation of Oligosaccharides

Oligosaccharide fractions were placed in 1.5 ml polypropylene tubes and treated with cold 48% aqueous hydrogen fluoride to make 5–10 µg/ml solution. Samples were kept for 18 hours at 4° C. and then aqueous HF was evaporated. The dephosphorylated samples were then rechromatographed on two Bio-Select SEC 125-5 HPLC columns connected in series using 0.05 M pyridinium acetate (pH 5.2).

EXAMPLE 6

Characterization of Product

The reactivity with monoclonal antibodies raised to the naturally occurring Hib LOS, as shown in Example 2, indicated that the product had the same immunochemical function as the naturally occurring Hib LOS. The samples were further analyzed by different techniques in order to determine structural identity to the desired complex carbohydrate.

a. Monosaccharide Composition Analysis.

Dephosphorylated oligosaccharide fractions were dissolved in 400 µl of 2 M trifluoroacetic acid and heated for 4 hours at 100° C. The hydrolysates were evaporated to dryness in a Speed-Vac concentrator, redissolved in 20 µl $H_2O$, and dried again Hydrolysates were analyzed by high-performance anion exchange chromatography with pulsed amperometrie detection using a Dionex BioLC system (Dionex, Sunnyvale, Calif.) with a CarboPac PA1 column.

b. Methylation Analysis.

Linkage analysis was performed on dephosphorylated oligosaccharide fractions using the microscale method modified for use with powdered NaOH. Partially methylated alditol acetates were analyzed by GC/MS in the El and Cl modes on a mass spectrometer.

c. Liquid Secondary Ion Mass Spectrometry (LSIMS).

LSIMS was performed using a mass spectrometer with a cesium ion source, Oligosaccharide samples (in 1 µl $H_2O$) were added to 1 µl of glycerol/thioglycerol (1:1) on a stainless steel probe tip. A Cs+ ion primary beam energy of 10 keV was used and the secondary sample ions were accelerated to 8 keV. Scans were taken in the negative-ion mode at 300 s/decade and recorded with an electrostatic recorder. The spectra were mass calibrated manually with Ultramark 1621 (PCR Research Chemicals, Inc., Gainesville, Fla.) to an accuracy of better than ±0.2 Da.

d. Electrospray Ionization Mass Spectrometer (ESI-MS).

Oligosaccharides and Odeacylated LPS were analyzed on a mass spectrometer with an electrospray ion source operating in the negative-ion mode. Oligosaccharide samples were dissolved in $H_2O$ mixed with running solvent (1 µl in 4 µl), and injected into a stream of $H_2O$/acetonitrlle (1/1, v/v) containing 1% acetic acid, at a flow rate of approx. 20 µl/min. Mass calibration was carried out with CsI in the negative-ion mode.

In some cases, selected oligosaccharide fractions were analyzed at higher resolving power (M/ΔM=2000) using a sector-orthogonal time of flight (TOF) instrument with an array detector operating under ESI conditions in the negative-ion mode. In this case, the solvent system and flow rate were essentially the same as described above for the quadrupole ESI experiments. A scan speed of 5 sec/decade was used for all samples over the m/z range of 500 to 3000 with an accelerating voltage of 4 kV and an ESI needle voltage of between 3.5–4 kV higher. Mass calibration was carried out with an external reference consisting of CsI taken under liquid secondary ion mass spectrometry conditions, followed by a one point correction of the doubly charged deprotonated molecular ion of the oligosaccharide from the LPS of *Salmonella typhimurium* Ra mutant ((M-2H)$^{2-}$ exact=973.2)) in the negative-ion ES-MS mode.

e. Matrix Assisted I,a.qer Desorption Ionization (MALDI) Mass Spectrometry.

O-Deacylated LPS samples were analyzed on a Voyager or an Elite MALDI-TOF instrument (PerSeptive Biosystems, Framingham, Mass.) equipped with a nitrogen laser (337 nM). All spectra were recorded in the negative-ion mode using delayed extraction conditions as described in detail elsewhere. (Gibson et al. J. Amer. Soc. Mass Spec. 8:645–658 (1997)). Samples were dissolved in H$_2$O (approx. 250 pmol/μl), and mixed 1:1 with the matrix solution (a saturated solution of 2,5-dihydroxybenzoic acid in acetone) and allowed to dry at room temperature on a gold-plated MALDI plate. Approximately 100 laser shots were recorded for each sample, averaged and then mass calibrated using an external mass calibrant consisting of renin substrate tetradecapeptide, insulin chain B, oxidized, and bovine insulin (all from Sigma). For external calibrations under these conditions, a mass accuracy of 0.1% was obtained For comparison purposes, a single point correction was made to the spectra of the O-deacylated LPS from PGEM using the expected lipid A fragments ion ((M-H) average=952.009), and then the spectra for the three chimeric strains were recalibrated using this lipid A fragment ion and an additional ion from PGEM (m/z 2835.7) present in all four samples.

f. Tandem Mass Spectrometry (MS/MS) Using Quadrupole-TOF (qTOF).

Dephosphorylated oligosaccharides were analyzed in the positive-ion mode on a mass spectrometer equipped with a nanospray ion source. The analyzer consists of a high pressure RF-only ion guide followed by a quadrupole mass filter. A high pressure quadrupole collision cell follows the first mass filter. The TOF mass analyzer is comprised of a reflection with an effective flight path of 2.5 meters. Samples were dissolved in H$_2$O/acetonitrile (1/1, v/v) containing 1% acetic acid, and 2 μl of each was injected into a nanospray tip. The nanospray needle voltage was typically 800–1000 V. One sample loading usually gave an analysis time of 30–40 min, which allowed a conventional mass spectrum to be obtained prior to the selection of several individual ions for CID) MS/MS. In MS mode the high resolution capability (8,000 FWHM) allowed unambiguous determination of the charge state for each ion. For CID-MS/MS operation the quadropole mass analyzer with a mass window of I m/z unit was used to select precursor ions for fragmentation, which in most cases were doubly charged (M+2H)$^{2+}$. The selected ions were fragmented in a collision cell with air as the coffision gas and analyzed in the orthogonal TOF operating at an accelerating potential of 20 kV. Fragment ion spectra were accumulated under computer control for periods of between 10 seconds and 1 minute. Mass assignments based on external calibration were generally within 50 ppm of calculated monoisotopic values whereas internal calibration gave masses accurate to +5 ppm.

g. SDS-PAGE Analysis of LPS.

Figure 2:
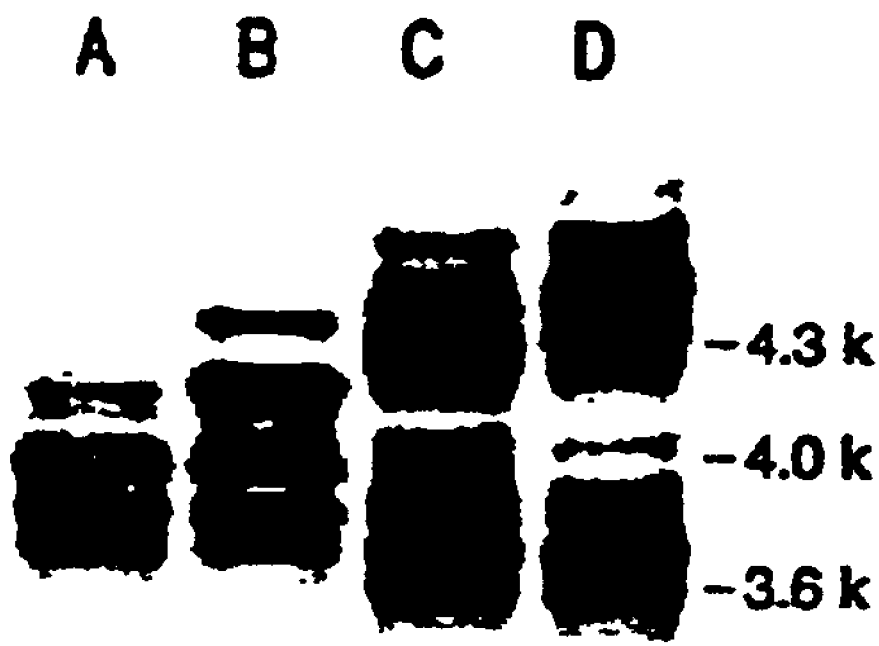
FIG. 2: SDS-PAGE of the LPS from *E. coli* strain JM 109 (designated pGEM) and the three chimeric strain, pGEMLOS-7, pGEMLOS-5, and pGEMLOS-4. The LPS range in molecular weight from ~3.3 to 5.5 kDa.

We have previously reported the transformation of *E. coli* strain JM 109 (a K-12 strain which produces rough LPS (r-LPS) which lack the O-side-chain) with a series of plasmids containing overlapping restriction fragments of DNA from the lsg region of *H. influenzae* type b strain A-2 (Kwaik et al, 1990). Partial LOS segments were produced. As diagrammned in FIG. 1, the pGEMLOS-4 clone contains all of the complete orfs (orfs A–G) in the lsg region, whereas pGEMLOS-5 contains orfs C–G, and pGEMLOS-7 contains orfs F–G. The clones pGEMLOS-4, pGEMLOS-5, and pGEMLOS-7 were shown by SDS-PAGE to produce modified LPS structures which added 1.4, 1.0, and 0.4 kDa moieties, respectively, to the 4.1 kDa *E. coli* core (FIG. 2).

h. Analysis of O-Deacylated LPS by MALDI-TOF.

For initial screening of LPS molecular weights and heterogeneity by mass spectrometry, small aliquots of LPS from PGEM, pGEMLOS-4, pGEMLOS-5, and pGEMLOS-7 were treated with anhydrous hydrazine to remove O-linked fatty acids from the lipid A moiety. The PGBM O-deacylated LPS sample contains several species in the range of 2738–3172 Da, representing the major *E. coli* core structures.

When fit to proposed compositions, the observed species were found to exhibit heterogeneity in heptose (Hep), hexose (Hex), 3-deoxy-D-mannooctulosonic acid (Kdo), phosphate (Phos), and phosphoethanolamine (PEA) (Table 2). Specifically, two main core types were observed containing either 3 Hex and 3 Hep (with 2 or 3 Kdos) or 4 Hex and 4 Hep (with 2 Kdos), with variable amounts of phosphate and PEA in both. The pGEMLOS-7 O-deacylated LPS mixture contained many of these same species, in addition to two major new species at (M-H)-3334.5 and 3456.8. The m/z 3334.5 species apparently arises from the addition of Hex and N-acetylhexosamine (HexNAc) to the PGEM core structure containing 4 Hex, 4 Hep, 2 Kdo, 2 Phos, and 1 O-deacylated diphosphorylated Lipid A (O-DPLA) moiety. A further addition of 1 PEA moiety gives the m/z 3456.8 species. These data suggest that the transformation producing pGEMLOS-7 results in the addition of a Hex-HexNAc moiety to the *E. coli* LPS. Likewise, the main species in the pGEMLOS-5 O-deacylated LPS (m/z 3700.6 and 3823.6) were found to arise from the addition of 2 Hex plus 2 HexNAc to the PGEM core structure containing 4 Hex, 4 Hep, 2 Kdo, 2 Phos, 1 O-DPLA, and 0 or 1 PEA (see Table 2). These structures are also found in the pGEMLOS-4 O-deacylated LPS, in addition to new species arising from the further addition of either another Hex (m/z 4083.2 and 4206.4) or HexNAc (m/z 4124.5 and 4246.8) to, in this case, the PGEM core structure containing 4 Hex, 4 Hep, 3 Kdo, 2 Phos, 1 O-DPLA, and 0 or 1 PEA (see Table 2). Of the chimeric LPS structures, only these high molecular weight pGEMLOS-4 components contained the third Kdo moiety.

i. Analysis of Oligosaccharides by ESI-MS and LSIMS.

The LPS from PGEM, pGEMLOS-4, pGEMLOS-5, and pGEMLOS-7 were subjected to mild acid hydrolysis to liberate free oligosaccharides. Initially, small aliquots of the oligosaccharide fractions were desalted by size exclusion HPLC and analyzed as mixtures by negative-ion ESI-MS. The ESI-MS spectra contained predominantly doubly charged ions, (M-2H)$^{2-}$. In general, the data were consistent with results from the MALDI-TOF analysis of O-deacylated LPS. The PGEM sample was found to contain seven major oligosaccharides and several minor species, ranging in molecular weight from 1459.3 to 2016.7 Da. As shown in Table 3, proposed compositions were determined for the various species which indicated that the structures consisted of two main core types; one containing 3 Hex, 3 Hep, and 1 Kdo, and another containing 4 Hex, 4 Hep, and 1 Kdo. Variability in the number of phosphate and PEA groups was responsible for the large number of species present in the mixture.

The pGEMLOS-4, pGEMLOS-5, and pGEMLOS-7 samples contained many of the species found in the PGEM sample, in addition to larger molecular weight oligosaccharides (Table 3). New LPS glycoforms of $M_r$ 2177.7 and 2302.5 were observed in the pGEMLOS-7 sample, consistent with the addition of a single Hex and HexNAc residue to the PGEM core structure containing 4 Hex, 4 Hep, 1 Kdo, 2 Phos, and 0 or 1 PEA. The high molecular weight components of the pGEMLOS-5 sample ($M_r$ 2543.9 and 2666.5) suggested the further addition of yet another Hex-HexNAc unit, and the pGEMLOS-4 sample contained even higher molecular weight materials (ranging from Mr 2706.1 to 2870.0) consistent with the addition of one more Hex or HexNAc moiety.

To aid in the determination of proposed compositions for these species, oligosaceeharides from the PGEM, pGEMLOS-4, pGEMLOS-5, and pGEMLOS-7 samples were separated by size exclusion chromatography and fractions were analyzed by LSIMS and/or ESI-MS. Selected fractions representing the two major PGEM core types and the various chimeric structures were then pooled, dephosphorylated with aqueous HF, rechromatographed on size-exclusion HPLC, and analyzed again by negative-ion LSIMS or ESI-MS. Proposed compositions for the molecular ions observed after HF-treatment are listed in Table 4. Upon removal of phosphate and PEA moieties, the major high mass species present in the pGEMLOS-7 sample is an oligosaccharide of $M_r$ (avg.) 2020.3 (1 HexNAc, 5 Hex, 4 Hep, and 1 Kdo). The pGEMLOS-5 sample contains an oligosaccharide of $M_r$ (avg.) 2386.3, resulting from the further addition of 1 Hex and 1 HexNAc to the pGEMLOS-7 LPS (2 HexNAc, 6 Hex, 4 Hep, and 1 Kdo). This species is also present in the pGEMLOS-4 sample, in addition to higher molecular weight structures containing an additional Hex ($M_r$(avg.) 2548.4) or HexNAc ($M_r$ (avg.) 2589.5).

j. Monosaccharide Composition and Linkage Analyses.

Mass spectrometry analyses of the free oligosaccharides from PGEM, pGEMLOS-4, pGEMLOS-5, and pGEMLOS-7 indicated that the different chimeric structures arise from additions of stoichiometric amounts of hexose and HexNAc residues to a variably phosphorylated PGEM core structure containing 4 Hex, 4 Hep, and 1 Kdo. No chimeric structures were observed to contain the 3 Hex, 3 Hep, and 1 Kdo core.

For comparison purposes, dephosphorylated oligosaccharide fractions containing the two PGEM core types and the main chimeric structures from pGEMLOS-4, pGEMLOS-5, and pGEMLOS-7 were hydrolyzed in 2N trifluoroacetic acid to determine their monosaccharide compositions, and therefore the identities of the Hex and HexNAc residues. When analyzed by high pH anion exchange chromatography with pulsed amperometric detection, the PGEM hydrolysates were found to contain only galactose, glucose, and L-glycero-D-manno-heptose (Table 5). (The Kdo residue is not recovered under these hydrolysis conditions.) The two core types were identified as $GalGlc_2Hep_3$ and $GalGc_3Hep_4$. The pGEMLOS-7 sample contained $GlcNH_2Gal_2Glc_3Hep_4$ (Table 5), suggesting that the larger PGEM core was being modified by the addition of one Gal and one N-acetylglucosamine (GlcNAc) residue. Likewise, the composition of the pGEMLOS-5 sample suggested that the larger PGEM core was being further glycosylated with only Gal and GlcNAc residues. Fraction 2 from pGEMLOS-4, which contained the same species as pGEMLOS-5, gave similar results, and fraction 1 from pGEMLOS-4, which contains three main species (see Table 4), contained slightly more GlcNH2.

Aliquots of the same six dephosphorylated oligosaccharide fractions used for monosaccharide composition analysis were taken for methylation analysis to establish sugar linkage positions. The partially methylated alditol acetates observed by GC/MS are listed in Table 6. Again, by comparing the two PGEM core types, it is relatively straightforward to see that the second terminal heptose of the larger PGEM core is converted to a 1,7-linked heptose in all of the chimeric structures and thus must represent the linkage site for the novel glycosylation. Since no chimeric structures were observed with the $Hep_3$ core, it is most likely that the nonreducing terminal heptose recently identified on the oligosaccharide branch in the K-12 core structure is the modified terminal heptose. Additionally, no new trilinked saccharides were obtained from the chimeric oligosaccharides, suggesting that the sugars were most likely all added in a straight chain.

k. Sequencing of Chimeric Oligosaccharides by MS/MS.

To confirm the identity of the linkage site between the *E. coli* LPS core and the novel oligosaccharide moieties, and to determine the sequences of the added sugars, the dephosphorylated oligosaccharides were subjected to MS/MS analysis. For these experiments, samples were run in the positive-ion mode and doubly charged molecular ions, $M+2H)^{2+}$, were selected for collision-induced dissociation (CID). Various reducing-terminal (Y-type) and nonreducing terminal (B-type) sequence ions are present in the spectra. For the PGEM oligosaccharide, the Y ion series including the $Y_{6\alpha'}$ (m/z 732.2 (2+)), $Y_{\alpha5'}$ (m/z 651.2 (2+)), and $Y_{4\alpha'}$ (m/z 1139.3) fragment ions, and the corresponding B ion series including the $B_{3\alpha'}$ (m/z 517.2), $B_{4\alpha'}$ (m/z 841.3), $B_5$ (m/z 1225.4), and $B_6$ (m/z 1417.4) fragment ions, support the published structure with the fourth heptose on the non-reducing terminus of the largest oligosaccharide branch. In addition to these sequence ions, several ions present in the spectrum apparently arise from internal cleavages, which can occur under high energy CID conditions. In the spectrum of the pGEMLOS-5 oligosaccharide, two similar Y and B-type ion series clearly define the sequence and linkage site of the added tetrasaccharide. Intense B ions at m/z 366.1 ($B_{2\alpha'}$) and 731.3 ($B_{4\alpha'}$) arise from the sequential cleavage of two Hex-HexNAc moieties. These losses are also represented by the corresponding $Y_{9\alpha'}$' (m/z 2020.6) and $_{7\alpha'}$ (m/z 1655.5) fragment ions. Fragment ions at m/z 923.3 ($B_{5\alpha'}$)0 and m/z 1463.4 ($Y_{6\alpha'}$) confirm that the Hex-HexNAc-Hex-HexNAc moiety is linked to a heptose, and additional cleavages further along the large oligosaccharide branch confirm that the novel tetrasaccharide is attached to the largest branch of the PGEM core structure.

In the MS/MS spectra of the chimeric oligosaccharides from pGEMLOS-7 and pGEMLOS-4, intense B ions also clearly defined the structures of the added sugar moieties. In the pGEMLOS-7 oligosaccharide ($M_r$ 2019.7), a B ion at m/z 366.1 corresponds to a single Hex-HexNAc disaccharide moiety. The pGEMLOS-4 oligosaccharide of $M_r$ 2587.9 ($HexNAc_3Hex_6Hep_4Kdo$) lost a HexNAc-Hex-HexNAc fragment (m/z 569.2) and a HexNAc-Hex-HexNAc-Hex-HexNAc fragment (m/z 934.3), whereas the pGEMLOS oligosaccharide of $M_r$ 2546.8 ($HexNAc_2Hex_7Hep_4 \rightarrow Kdo$) lost a Hex-Hex-HexNAc (m/z 528.2) and a Hex-Hex-HexNAc-Hex-HexNAc (m/z 893.3,) fragment. In addition to those B-type ions, the latter spectrum also contained large ions at m/z 366.1 and 731.3, which apparently arise as internal fragments in that case.

Figure 3:
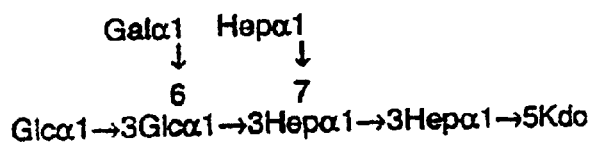
FIG. 3: Proposed structures of the chimeric oligosacclarides. Only the complete *E. coli* K-12 core structure containing a fourth heptose on the terminus of the oligosaccharide branch undergoes modification. Additional saccharides (designated R) are added to the 7-position of this heptose to form the chimeric oligosaccharides.
Figure 3:
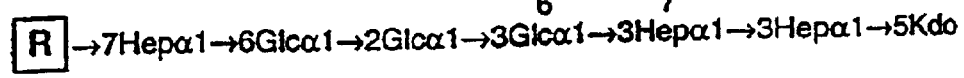
Figure 3:
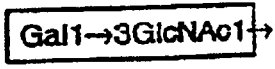
Figure 3:
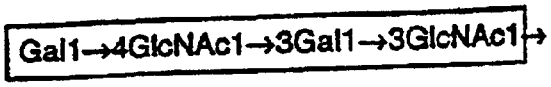
Figure 3:
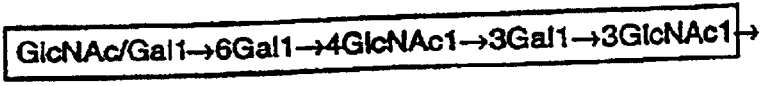

Assuming that the oligosaccharides are built up sequentially, i.e., from pGEMLOS-7 to pGEMLOS-5 to pGEMLOS-4, the MS/MS data, in combination with our methylation analysis results, allows the partial structures of the chimeric oligosaccharides to be deduced as shown in FIG. 3.

The structural data support the prediction that *E. coli* K-12 transformed with plasmids containing portions of an eight gene segment from *H. influenzae* involved in LOS biosynthesis makes chimeric LPS which can be modified to produce oligosaccharide essentially identical to that of *H. influenzae*. Moreover, we have shown that the chimeric LPS are segregated hybrid-type structures, where the *E. coli* R-LPS core structure is first synthesized and then serves as a scaffold for *H. influenzae* LOS biosynthesis enzymes to add a second independent set of sugars not found in the parent *E. coli* strain. Thus, the biosynthetic pathways appear to be sequential (segregated) and not intermixed.

Before this invention was made, the role of the terminal branch heptose in the *E. coli* R-LPS as the acceptor for oligosaccharide elongation or the requirement for a functional initiator enzyme was unknown. The published structure for the complete *E. coli* K-12 core did not contain a second terminal heptose, but rather had this fourth heptose as part of the inner core region. The oligosaccharide branch was believed to terminate in glucose, which was proposed to be the acceptor site for O-antigen and other substituents. The role of the initiator enzyme was unknown. It is now apparent that only *E. coli* R-LPS structures containing this fourth heptose (i.e., complete core structures) underwent elongation in the plasmid-transformed chimeric strains and thus, only those *E. coli* having this composition are useful as production cells for the production of *H. influenzae*. In the chimeric structures, GlcNAc is the first sugar added to the seven position of this heptose. There are two possible explanations for this crucial first step in the elongation sequence. One, an N-acetylglucosamine-specific glycosyltransferase from Haemophilus encoded in orff or orfg either has this precise specificity or is promiscuous enough to allow this reaction to occur. Two, some analogous *E. coli* glycosyltransferase gene is being activated by a Haemophilus regulatory gene. Since sequence comparisons of the seven genes contained in this plasmid suggest that both glycosyltransferase and regulatory genes are present, both explanations are possible. However, the fact that terminal GlcNAc and 1,7-linked heptose have been found in nonstoichiometric amounts in some other strains of *E. coli* K-12 suggests that the addition of this sugar to the terminus of the oligosaccharide branch is accomplished by *E. coli* enzymes. It was recently reported that when mutations causing the rough phenotype in *E. coli* K-12 are complemented, the complemented strains produce an O-antigen which has GlcNAc at the reducing terminus of the repeat unit. Regardless of the mechanism of this first key step in the extension of the PGEM core, it appears that addition of this GlcNAc is rate-limiting, since a large percentage of unmodified PGEM core R-LPS remains in the chimeric mixtures Furthermore, very little or no intermediate structures are observed as one progresses from pGEMLOS-7 to pGEMLOS-5 and pGEMLOS-4, suggesting that once this first GlcNAc is added, the addition of the other Haemophilus-related sugars proceeds quickly to defined end points. If other steps in the biosynthesis of the chimeric LPS were as incomplete as the addition of this first GlcNAc, one would expect to see these other intermediate structures, yet none were observed. Therefore, it is likely that a N-acetylglucosaminyltransferase from *E. coli* that is regulated through the product of orff or orfg adds this first key sugar in the chimeric structures. Preliminary data on a chimeric construct containing orfg alone showed a mass shift of 203 Da (HexNAc), suggesting that orfg encodes this regulatory gene.

The second step in the biosynthesis of the chimeric LPS is the addition of galactose to the 3-position of the terminal GlcNAc. The resulting disaccharide, Gall3GlcNAc, is the structural moiety observed in pGEMLOS-7, which arises when the transforming plasmid contains orfs F–G from Haemophilus. Examination of the predicted amino acid sequences of the gene products indicates that orfF has high homology (66% identity) to a galactosyltransferase (asmE) from *Erwinia amylovora*, suggesting that it may encode a galactosyltransferase in Haemophilus. OrfG does not show any homology to known oligosaccharide biosynthetic genes, but is homologous (64% identity) to a gene encoding the ModE protein in *E. coli*. This protein is involved in molybdenum transport and regulation of transcription, suggesting that orfG may encode a regulatory protein from Haemophilus (which may be regulating an N-acetylglucosaminyltransferase gene from *E. coli* in the chimeric strains).

In the pGEMLOS-5 strain, an additional three genes are contained in the transforming plasmid (orfs C–G) and an additional GlcNAc and Gal are observed in the resulting LPS. These sugars now define the tetrasaccharide Gall-4GlcNAc-3Gall3GlcNAc. The LPS from this transformant is now reactive to the 3F11 MAb, suggesting that this new disaccharide is betalinked to form the terminal trisaccharide, Gall4GlcNAcl-3Gal. All of the new orfs contained in this plasmid have some homology with known glycosyltransferase genes: orfC has homology with the asmD (26% identity) from *Erwinia amylovora*, which encodes a glycosyltransferase for exopolysaccharide synthesis, and TrsD (38% identity) from *Yersina entercolitica*, a gene involved in LPS inner core synthesis, orfD has homology with the sialyltransferase gene (lst) (27% identity) from *Neisseria gonorrhoeae*, and orfE has homology with a putative glycosyltransferase gene (77% identity) from Actinobacillus sp. and the galactosyltransferase gene, amsB (27% identity) from *Erwinia amylovora*. The fact that these three additional orfs in the transforming plasmid apparently result in the addition of only two more sugars to the growing oligosacchazide chain may indicate that the acceptor for one of the glycosyltransferases is absent in the chimeric LPS.

When two more orfs are added in the transforming plasmid (orfs A–G) to form the pGEMLOS-4 chimeric strain, we observe that the 3F11 epitope disappears and the terminal Gal residue of the epitope is capped by either a second Gal or a GlcNAc moiety, apparently linked to the 6-position of the GaL. These new species present in the pGEMLOS-4 LPS population were also observed to contain a third Kdo moiety, presumably somewhere in their core regions. While some of the incomplete core structures found in the wild-type *E. coli* K-12 LPS populations also contain a third Kdo, of the chimeric structures, only the structures unique to pGEMLOS-4 were found to contain a third Kdo. This chimeric strain was also recognized by MAb 6E4 which recognizes an inner core, Kdo-related epitope in *H. influenzae*, suggesting that this third Kdo forms a different epitope than the one found in the core structure of the wild-type *E. coli* LPS. Thus, the addition of orfs A and B to the transforming plasmid which formed strain pGEMLOS-4 seems to have multiple effects on the chimeric LPS structure. OrfB is homologous (46% identity) to the sialyltransferase gene from *N. gonnorhea*. OrfA is homologous to both the Rfb X gene product (22% identity) from *E. coli* and TrsA (24% identity) of *Y. entercolitica*. These are putative O-antigen transporters (36,37), suggesting that orfA may encode a flippase.

While sialyl-N-acetyllactosamine-containing structures are only minor components of the wild-type *H. influenzae* type b strain A2 LOS population, we have previously seen that lsg genes are involved in the synthesis of this epitope. Transposon mutagenesis of orfD) produced mutant strain 281.25, that lost all ability to add galactose to Hib LOS glycoforms. This strain could not make any of the wild-type LOS structures larger than the major species containing four glucoses and three heptoses. Mutation of orfE (which is downstream of orfD) produced strain 276.4 which had essentially the same defect, except for one important difference: strain 276.4 retained the ability to make the sialyl-N-acetyllactosamine epitope. These results suggest that in the transposon mutants, the knockout of orfD has a polar effect on orfE, which would imply that the gene product of orfE is a galactosyltransferase required for synthesis of the higher molecular weight wild-type structures containing terminal galactose(s) on their glucose disaccharide branches and the gene product of orfD is likely an N-acetylglucosaminyltransferase required for the synthesis of the sialyl-N-acetyllactosamine epitope. The case for these assignments can be made on the basis of the homologies noted above (orfE is homologous to a galactosyltralsferase gene) and the LOS glycoforms observed in the 276.4 and 281.25 mutant strains. Since no truncated versions of the sialyl-N-acetyllactosamine structure were seen in the 276.4 LOS population (i.e.; no species lacking either sialic acid or sialic acid plus galactose), it seems probable that the orfd gene codes for the glycosyltransferase which adds the GlcNAc to the oligosaccharide branch. This is also consistent with the observation that one of the genes in orfd C–E is apparently responsible for adding GlcNAc to the 3-position of the Gal which is terminal in the pGEMLOS-7 LPS structure.

This chimeric carbohydrate expression system has provided information that is relevant to unraveling the functions of these lsg genes and has the additional advantage of being carried out in the absence of the normal endogenous genetic background on *H. influenzae*. Indeed, while gene knockouts of some of the lsg genes in *H. influenzae* have been completed, downstream or regulatory gene effects can often complicate their functional analysis. In this *E. coli* expression system, structural analysis of the resulting chimeric LPS has shown that synthesis proceeded as a serial (non-parallel) synthesis, that is, the new elements of the chimeric LPS were added after the formation of the *E. coli* R-LPS. The fact that this synthesis was sequential (rather than interdigitated with the R-LPS synthesis, for example) allowed for the functions of these *H. influenzae* gene products to be more readily delineated from the chimeric oligosaccharide structures. Moreover, screening of the chimeric LPS products with monoclonal antibodies enabled us to follow the formation of terminal sugar sequences (epitopes) that are unique to the Haemophilus strain from which the plasmid DNA originated.

All publications and patents cited herein are incorporated by reference as though fully set forth.

This invention has been described with respect to specific examples and embodiments. However, it is understood that one skilled in the art may make variations or modifications that are within the spirit and scope of the invention.

TABLE 1

Bacterial Strains, LPS and Vectors

| Strain/Plasmid | Relevant characteristics | Reference/source |
|---|---|---|
| *E. coli* | | |
| JM109 | recA, supE, hsR, Δ(lac-pro) | (40) |
| *H. influenzae* | | |
| A2 | Parental strain | (10) |
| Plasmid | | |
| pGEM3Zf+ | Ap$^R$ | Promega Biotech |
| pGEMLOS-4 | Ap$^R$, contains 7.4 kb bamHI-pstI DNA *H. influenzae* lsg locus | This study |
| pGEMLOS-5 | Ap$^R$, contains 5.5 kb hindIII-pstI DNA *H. influenzae* lsg locus | This study |
| pGEMLOS-7 | Ap$^R$, contains 2.8 kb sphI-pstI DNA *H. influenzae* lsg locus | This study |
| LPS | | |
| pGEM | isolated from strain JM109 transformed with pGEM3zf+ | This study |
| pGEMLOS-4 | isolated from strain JM109 transformed with the plasmid pGEMLOS-4 | This study |
| pGEMLOS-5 | isolated from strain JM109 transformed with the plasmid pGEMLOS-5 | This study |
| pGEMLOS-7 | isolated from strain JM109 transformed with the plasmid pGEMLOS-7 | This study |

TABLE 2

Molecular weights ($M_r$) and proposed compositions of the O-deacylated LPS from pGEM, pGEMLOS-7, pGEMLOS-5, and pGEMLOS-4$^a$

| pGEM | pGEMLOS-7 | pGEMLOS-5 | pGEMLOS-4 | Calc. $M_r$ | Proposed compositions | | | | | | |
|---|---|---|---|---|---|---|---|---|---|---|---|
| | | | 4247.8 (40) | 4247.6 | 3HexNAc | 6Hex | 4Hep | 2Phos | 1PEA | 3Kdo | 1O-DPLA |
| | | | 4207.4 (26) | 4206.6 | 2HexNAc | 7Hex | 4Hep | 2Phos | 1PEA | 3Kdo | 1O-DPLA |
| | | | 4125.5 (46) | 4124.6 | 3HexNAc | 6Hex | 4Hep | 2Phos | | 3Kdo | 1O-DPLA |
| | | | 4084.2 (27) | 4083.6 | 2HexNAc | 7Hex | 4Hep | 2Phos | | 3Kdo | 1O-DPLA |
| | | 3947.4 (38) | | 3947.3 | 2HexNAc | 6Hex | 4Hep | 2Phos | 2PEA | 2Kdo | 1O-DPLA |
| | | 3904.4 (25) | | 3904.3 | 2HexNAc | 6Hex | 4Hep | 2Phos | 1PEA | 2Kdo | 1O-DPLA |
| | | 3824.6 (100) | 3824.4 (40) | 3824.3 | 2HexNAc | 6Hex | 4Hep | 2Phos | 1PEA | 2Kdo | 1O-DPLA |
| | | 3701.6 (90) | 3701.3 (100) | 3701.2 | 2HexNAc | 6Hex | 4Hep | 2Phos | | 2Kdo | 1O-DPLA |
| | | 3603.8 (31) | 3603.6 (26) | 3604.1 | 2HeXNAc | 6Hex | 4Hep | 2Phos | 1PEA | 1Kdo | 1O-DPLA |

TABLE 2-continued

Molecular weights (M$_r$) and proposed compositions of the O-deacylated LPS from pGEM, pGEMLOS-7, pGEMLOS-5, and pGEMLOS-4[a]

| pGEM | pGEMLOS-7 | pGEMLOS-5 | pGEMLOS-4 | Calc. M$_r$ | Proposed compositions | | | | | | |
|---|---|---|---|---|---|---|---|---|---|---|---|
| | 3457.8 (41) | | | 3458.9 | 1HexNAc | 5Hex | 4Hep | 2Phos | 1PEA | 2Kdo | 1O-DPLA |
| | 3335.5 (43) | | | 3335.9 | 1HexNAc | 5Hex | 4Hep | 2Phos | | 2Kdo | 1O-DPLA |
| 3172.7 (43) | | | | 3173.6 | | 4Hex | 4Hep | 3Phos | 1PEA | 2Kdo | 1O-DPLA |
| 3093.2 (97) | 3093.5 (74) | 3094.0 (42) | | 3093.6 | | 4Hex | 4Hep | 2Phos | 1PEA | 2Kdo | 1O-DPLA |
| 3050.4 (67) | | | | 3050.6 | | 4Hex | 4Hep | 3Phos | | 2Kdo | 1O-DPLA |
| 2970.1 (100) | 2970.6 (100) | 2970.8 (68) | | 2970.6 | | 4Hex | 4Hep | 2Phos | | 2Kdo | 1O-DPLA |
| 2958.5 (90) | 2958.8 (76) | 2959.5 (87) | 2960.2 (60) | 2959.5 | | 3Hex | 3Hep | 2Phos | 1PEA | 3Kdo | 1O-DPLA |
| | | 2941.9 (56) | | 2942.3 | | 3Hex | 3Hep | 3Phos | 2PEA | 2Kdo | 1O-DPLA |
| 2836.7 (87) | 2836.7 (68) | 2836.7 (90) | 2836.7 (99) | 2836.4 | | 3Hex | 3Hep | 2Phos | | 3Kdo | 1O-DPLA |
| | | 2819.2 (70) | 2818.8 (49) | 2819.3 | | 3Hex | 3Hep | 3Phos | 1PEA | 2Kdo | 1O-DPLA |
| 2738.4 (40) | 2738.8 (41) | 2739.0 (62) | 2738.7 (54) | 2739.3 | | 3Hex | 3Hep | 2Phos | 1PEA | 2Kdo | 1O-DPLA |
| | | 2616.5 (39) | 2616.2 (39) | 2616.2 | | 3Hex | 3Hep | 2Phos | | 2Kdo | 1O-DPLA |

[a]Relative ion abundances are given in parentheses. Species above the dashed line are chimeric structures.

TABLE 3

Molecular weights (M$_r$) and compositions of the oligosaccharides from pGEM, pGEMLOS-7, pGEMLOS-5, and pGEMLOS-4[a]

| pGEM | pGEMLOS-7 | pGEMLOS-5 | p-GEMLOS-4 | Calc. M$_r$ | Proposed compositions | | | | | |
|---|---|---|---|---|---|---|---|---|---|---|
| | | | 2870.0 (12) | 2870.8 | 3HexNAc | 6Hex | 4Hep | 2Phos | 1PEA | 1Kdo |
| | | | 2828.6 (10) | 2827.8 | 3HexNAc | 6Hex | 4Hep | 3Phos | | 1Kdo |
| | | | 2747.8 (13) | 2747.8 | 3HexNAc | 6Hex | 4Hep | 2Phos | | 1Kdo |
| | | | 2706.1 (12) | 2706.8 | 2HexNAc | 7Hex | 4Hep | 2Phos | | 1Kdo |
| | | 2666.5 (20) | 2666.7 (13) | 2667.7 | 2HexNAc | 6Hex | 4Hep | 2Phos | 1PEA | 1Kdo |
| | | 2543.9 (58) | 2544.0 (31) | 2544.7 | 2HexNAc | 6Hex | 4Hep | 2Phos | | 1Kdo |
| | 2302.5 (30) | | | 2302.6 | 1HexNAc | 5Hex | 4Hep | 2Phos | 1PEA | 1Kdo |
| | 2177.7 (45) | | | 2179.6 | 1HexNAc | 5Hex | 4Hep | 2Phos | | 1Kdo |
| | | 2058.6 (23) | | 2060.5 | | 4Hex | 4Hep | 2Phos | 2PEA | 1Kdo |
| 2016.7 (13) | | | | 2017.4 | | 4Hex | 4Hep | 3Phos | 1PEA | 1Kdo |
| 1937.2 (50) | 1937.1 (52) | 1937.1 (15) | | 1937.5 | | 4Hex | 4Hep | 2Phos | 1PEA | 1Kdo |
| 1893.5 (51) | | | | 1894.4 | | 4Hex | 4Hep | 3Phos | | 1Kdo |
| 1814.0 (100) | 1814.0 (54) | 1814.0 (19) | | 1814.4 | | 4Hex | 4Hep | 2Phos | | 1Kdo |
| | 1743.9 (19) | | | 1745.4 | | 4Hex | 3Hep | 2Phos | 1PEA | 1Kdo |
| | 1705.8 (24) | 1705.9 (11) | 1705.8 (14) | 1706.4 | | 3Hex | 3Hep | 2Phos | 2PEA | 1Kdo |
| | 1622.4 (15) | 1622.5 (14) | | 1622.4 | | 4Hex | 3Hep | 2Phos | | 1Kdo |
| 1582.9 (49) | 1582.8 (100) | 1582.8 (53) | 1582.9 (68) | 1583.4 | | 3Hex | 3Hep | 2Phos | 1PEA | 1Kdo |
| 1539.2 (51) | | 1539.3 (16) | 1539.3 (19) | 1540.3 | | 3Hex | 3Hep | 3Phos | | 1Kdo |
| 1459.3 (78) | 1459.9 (50) | 1459.9 (100) | 1459.8 (100) | 1460.3 | | 3Hex | 3Hep | 2Phos | | 1Kdo |

[a]Relative ion abundances (given in parentheses) represent the sum of the monoisotopic molecular ion and anhydro peaks for a given species (see FIG. 4). Components listed above the dashed line are chimeric structures.

TABLE 4

Molecular weights (M$_r$) and proposed compositions of the dephosphorylated oligosaccharides from pGEM, pGEMLOS-7, pGEMLOS-5, and PGEMLOS-4[a]

| Fraction | Obs. M$_r$ (avg.) | Calc. M$_r$ (avg.) | Calc. M$_r$ (exact) | Proposed compositions | | | |
|---|---|---|---|---|---|---|---|
| pGEM (Fr. 2) | 1300.8 | 1301.1 | 1300.4 | | 3Hex | 3Hep | 1Kdo |
| pGEM (Fr. 1) | 1655.3 | 1655.4 | 1654.5 | | 4Hex | 4Hep | 1Kdo |
| pGEMLOS-7 | 2020.3 | 2020.8 | 2019.7 | 1HexNAc | 5Hex | 4Hep | 1Kdo |
| pGEMLOS-5 | 2386.3 | 2386.1 | 2384.8 | 2HexNAc | 6Hex | 4Hep | 1Kdo |
| pGEMLOS-4 (Fr. 2) | 2386.3 | 2386.1 | 2384.8 | 2HexNAc | 6Hex | 4Hep | 1Kdo |
| pGEMLOS-4 (Fr. 1) | 2386.1 | 2386.1 | 2384.8 | 2HexNAc | 6Hex | 4Hep | 1Kdo |
| | 2548.4 | 25482 | 2546.8 | 2HexNAc | 7Hex | 4Hep | 1Kdo |
| | 2589.5 | 2589.3 | 2587.9 | 3HexNAc | 6Hex | 4Hep | 1Kdo |

[a]Observed molecular weights are reported as average mass values.

TABLE 5

Monosaccharide compositions of the dephosphorylated oligosaccharide fractions[a]

| | pGEM (Fr. 2) | pGEM (Fr. 1) | pGEM-LOS-7 | pGEM-LOS-5 | pGEM-LOS-4 (Fr. 2) | pGEM-LOS-4 (Fr. 1) |
|---|---|---|---|---|---|---|
| GlcN | | | 1.0 | 2.7 | 2.4 | 3.3 |
| Gal | 0.9 | 1.1 | 1.7 | 3.0 | 2.8 | 3.1 |
| Glc | 2.2 | 3.2 | 3.2 | 3.4 | 3.4 | 3.4 |
| Hep | 3.0 | 4.0 | 4.0 | 4.0 | 4.0 | 4.0 |

[a]Molar ratios were derived from comparison to the hydrolysate of the *S. typhimurium* Ra oligosaccharide of known composition, and then those values were normalized to either 3.0 or 4.0 heptoses in each fraction.

TABLE 6

Methylation analysis of the dephosphorylated oilgosaccharide fractions[a]

| | pGEM (Fr. 2) | pGEM (Fr. 1) | pGEM-LOS-7 | pGEM-LOS-5 | pGEM-LOS-4 (Fr. 2) | pGEM-LOS-4 (Fr. 1) |
|---|---|---|---|---|---|---|
| T-Glc | 0.5 | 0.2 | | | | |
| T-Gal | 0.6 | 0.5 | 1.2 | 0.9 | 0.7 | 0.7 |
| 1,2-Glc | 0.2 | 0.7 | 1.0 | 0.8 | 0.8 | 0.7 |
| 1,3-Gal | | | | 0.4 | 0.5 | 0.6 |
| 1,6-Glc | 0.4 | 1.1 | 1.6 | 1.5 | 1.3 | 1.3 |
| 1,6-Gal | | | | | 0.3 | 0.6 |
| 1,3,6-Glc | 1.0 | 1.0 | 1.0 | 1.0 | 1.0 | 1.0 |
| T-Hep | 0.3 | 0.6 | 0.6 | 0.3 | 0.3 | 0.2 |
| 1,3-Hep | 0.3 | 0.3 | 0.3 | 0.4 | 0.6 | 0.4 |
| 1,7-Hep | | | 0.4 | 0.6 | 0.5 | 0.6 |
| 1,3,7-Hep | 0.4 | 0.4 | 0.2 | 0.3 | 0.5 | 0.5 |
| T-GlcNAc | | | 0.1 | 0.2 | 0.2 | 0.3 |
| 1,4-GlcNAc | | | | 0.9 | 1.1 | 1.0 |
| 1,3-GlcNAc | | | 0.3 | 0.7 | 0.7 | 1.0 |

[a]Peak areas were measured from the GC/MS EI total ion chromatograms, and values were normalized to the 1,3,6-glc residue. The data for pGEMLOS-7 are the average of two runs.

Gene Homology Table

| Lsg | Homologous Genes/ Proteins | Ref. | Protein Homology | Protein Function | Proposed Function(s) of Haemophilus Gene Product |
|---|---|---|---|---|---|
| LsgA | Wzx from *Escherichia coli* | (1) | 22% identity 44% positive | putative O-antigen transporter | flippase?[a] |
| | TrsA from *Yersinia enterocolitica* | (2) | 24% identity 44% positive | putative O-antigen transporter | |
| | Wzx from *Bacteroides fragilis* | (3) | 20% identity 36% positive | putative O-antigen flippase | |
| LsgB | sialyltransferase gene from *Neisseria meningitidis* | (4) | 27% identity 46% positive | α-2,3-sialyltransferase | sialyltransferase or other glycosyltransferase[b] |
| LsgC | AmsD from *Erwinia amylovora* | (5) | 26% identity 47% positive | galactosyltransferase | 1,4-galactosyltransferase |
| | TrsD from *Y. enterocolitica* | (6) | 38% identity 52% positive | involved in LPS inner core synthesis | |
| LsgD | LgtE from *Neisseria gonorrhoeae* | (7) | 22% identity 40% positive | lacto-N-neotetraose glycosyltransferase | 1,3-N-acetylglucosaminyl-transferase[c] |
| | LgtB from *N. gonorrhoeae* and *N. meningitidis* | (8) | 24% identity 41% positive | lacto-N-neotetraose glycosyltransferase | |
| LsgE | putative glycosyltransferase gene from *Actinobacillus* sp. | (9) | 77% identity 84% positive | putative glycosyltransferase | galactosyltransferase[d] |
| | AmsB from *E. amylovora* | (5) | 27% identity 49% positive | galactosyltransferase | |
| | LgtD from *Rickettsia prowazekii* | (10) | 23% identity 47% positive | glycosyltransferase | |
| LsgF | AmsD from *E. amylovora* | (5) | 45% identity 66% positive | galactosyltransferases | 1,3-galactosyltransferase |
| | putative deoxy-L-talan synthesis gene from *Actinobacillus* sp. | (11) | 83% identity 90% positive | glycosyltransferase | |
| | GDP-mannose biosynthesis gene from *E. coli* | (12) | 37% identity 54% positive | glycosyltransferase | |

-continued

Gene Homology Table

| Lsg | Homologous Genes/ Proteins | Ref. | Protein Homology | Protein Function | Proposed Function(s) of Haemophilus Gene Product |
|---|---|---|---|---|---|
| LsgG | ModE from *E. coli* | (13) | 47% identity 64% positive | molybdenum transport and regulation of transcription | regulation or modulation of the *E. coli* wecA gene, which results in the addition of GlcNAc to the branch heptose |
| | MopB from *Rhodobacter capsulatus* | (14) | 32% identity 51% positive | molybdenum-pterin-binding protein | |

[a]When lsgA and lsgB are both present, the pGEMLOS-5 tetrasaccharide structure can be extended with either a 6-linked galactose or GlcNAc to form the structures seen in pGEMLOS-4 LPS, which also contain a third Kdo moiety which may be the epitope recognized by MAb 6E4. Thus, the unctions of these two Haemophilus orfs remain unclear.
[b]Recent studies with a double gene knockout of lst, a gene with high homology to the sialyltransferase in *Haemophilus ducreyi* (15), and lsgB suggest that lsgB may also encode a sialyltransferase.
[c]The structure of the pGEMLOS-5 LPS suggests that one of the three orfs, C, D, or E encodes a 1,3-N-acetylglucosaminyltransferase and another encodes a 1,4-galactosyltransferase. Based on our previous investigations of the LOS formed when lsgD or lsgE are knocked out in mutant strains 281.25 and 276.4, respectively (16), we can conclude that lsgD is likely to encode a 1,3-N-acetylglucosaminyltransferase and lsgC and lsgE are both likely to encode galactosyltransferases.
[d]The LOS formed when lsgE is knocked out (16) suggest that lsgE encodes a galactosyltransferase whose acceptor may be absent in the chimeric LPS.

References for Gene Homology Table
1. Yao, Z., and Valvano, M. A., J. Bacteriol., 176, 4144–4156 (1994).
2. Zhang, L., Radziejewska-Lebrecht, J. Krajewska-Pietrasik, D., Toivanen, P., and Skurnik, M., Mol. Microbiol., 23,(1), 63–76 (1997).
3. Comstock, L. E., Coyne, M. J., Tzianabos, A. O., Pantosti, A., Onderdonk, A. B., and Kasper, D. L., Infect. Immun., 67(7), 3525–3532 (1999).
4. Gilbert, M., Watson, D. C., Cunningham, A. M., Jennings, M. P., Young, N. M., and Wakarchuk, W. W., J. Biol. Chem., 271,(45), 28271–28276 (1996).
5. Bugert, P., and Geider, K., Mol. Microbiol., 15(5), 917–933 (1995).
6. Skurnik, M., Venho, R., Toivanen, P., and al-Hendy. A., Mol. Microbiol., 17(3), 575–594 (1995).
7. Gotschlich, E. C., J. Exp. Med., 180(6), 2181–2190 (1994).
8. Jennings, M. P., Hood, D. W., Peak, I. R., Virji, M., and Moxon, E. R., Mol. Microbiol, 18(4), 729–740 (1995).
9. Yoshida, Y., Nakano, Y., Yamashita, Y., and Koga, T., Infect. Immun., 66, 107–114 (1998).
10. Andersson, S. G., Zomorodipour, A., Andersson, J. O., Sicheritz-Ponten, T., Alsmark, U.C., Podowski, R. M., Naslund, A. K., Eriksson, A. S., Winkler, H. H., and Kurland, C. G., Nature, 396(6707), 133–140 (1998).
11. Nakano, Y., Yoshida, Y., Yamashita, Y., and Koga, T., Biochim. Biophys. Acta, 1442(2–3), 409–414 (1998).
12. Marolda, C. L., and Valvano, M. A., J. Bacteriol., 177(19), 5539–5546 (1995).
13. Grunden, A. M., Ray, R. M., Rosentel, J. K., Healy, R. G., and Shanmugam, K. T., J. Bacteriol., 178(3), 735–744 (1996).
14. Wang, G., Angermuller, S., and Klipp, W., J. Bacteriol., 175(10), 3031–3042 (1993).
15. Bozue, J. A., Tullius, M. V., Wang, J., Gibson, B. W., and Munson, R. S., Jr., J. Biol. Chem., 274(7), 4106–4114 (1999).
16. Phillips, N. J., McLaughlin, R., Miller, T.J., Apicella, M. A., and Gibson, B. W., Biochemistry, 35, 5937–5947 (1996).

What is claimed is:

1. A transformed Salmonella bacterium for use as a chimeric carbohydrate production cell, wherein the bacterium comprises:
   (a) a lipooligosaccharide (LOS) or lipopolysaccharide (LPS) comprising a core region containing a terminal heptose;
   (b) a DNA sequence comprising an rfe gene; and
   (c) an isolated DNA sequence comprising a lipooligosaccharide-synthesis gene G (lsgG) from *Haemophilus influenzae*, wherein lsgG encodes LsgG, and wherein the rfe is regulated by LsgG such that a *H. influenzae*-specific Los is synthesized by the addition of an acceptor molecule to the terminal heptose.

2. The bacterium of claim 1, which is *Salmonella minnesota*.

3. The bacterium claim 1, which has terminal heptose on a kdo core.

4. The bacterium of claim 1, wherein the acceptor molecule is N-acetyl glucosamine.

5. The bacterium of claim 1, wherein the LOS or LPS is an *Haemophilus influenzae*, Neisseria spp. or Salmonella spp.-specific LOS or LPS.

6. A process for producing a complex carbohydrate, which comprises the steps of:
   (a) inoculating production cells which are bacteria according to claim 1 into a culture medium capable of supporting the growth of said production cells;
   (b) allowing the growth of said production cells; and
   (c) recovering the complex carbohydrate from the culture medium.

7. The process of claim 6, which comprises the steps of extracting chimeric lipoligosaccharide or lipopolysaccharide from the cultured cells, hydrolysing the extracted lipoologosaccharide or lipopolysaccharide, and recovering the resulting oliposaccharide or polysaccharide.

* * * * *

UNITED STATES PATENT AND TRADEMARK OFFICE
CERTIFICATE OF CORRECTION

PATENT NO. : 6,743,607 B2
DATED : June 1, 2004
INVENTOR(S) : Michael A. Apicella, Bradford W. Gibson and Nancy J. Phillips It is certified that error appears in the above-identified patent and that said Letters Patent is hereby corrected as shown below:

Title page,
Item [63], Related U.S. Application Data, after "May 18, 2000" please insert
-- and application no. 09/574,460 filed on May 18, 2000 --;
Item [56], References Cited, FOREIGN PATENT DOCUMENTS, please insert
-- WO 98/50557         11/1998         PCT --
OTHER PUBLICATIONS, "Skurnik et al." reference, please delete "N." and insert
-- M. -- therefor;
"Swierzko et al." reference, please delete "3316-3221" and insert -- 3216-3221 --
therefor;

Column 21,
Line 58, after "bacterium" please insert -- of --;

Column 22,
Line 56, please delete "lipoligosaccharide" and insert -- lipooligosaccharide -- therefor;
Line 59, please delete "oliposaccharide" and insert -- oligosaccharide -- therefor.

Signed and Sealed this

Fifteenth Day of March, 2005

JON W. DUDAS
*Director of the United States Patent and Trademark Office*